(12) United States Patent
Coggins

(10) Patent No.: US 11,554,030 B2
(45) Date of Patent: Jan. 17, 2023

(54) PROSTHETIC LIMB FITTING APPARATUS FOR PREDICTING THE EFFECT OF A PROPOSED PROSTHETIC LIMB ON ABLE JOINTS

(71) Applicant: Joseph Coggins, Irvine, CA (US)

(72) Inventor: Joseph Coggins, Irvine, CA (US)

( * ) Notice: Subject to any disclaimer, the term of this patent is extended or adjusted under 35 U.S.C. 154(b) by 0 days.

(21) Appl. No.: 16/741,654

(22) Filed: Jan. 13, 2020

(65) Prior Publication Data

US 2020/0323659 A1    Oct. 15, 2020

Related U.S. Application Data

(63) Continuation of application No. 14/721,169, filed on May 26, 2015, now Pat. No. 10,531,968.

(60) Provisional application No. 62/002,722, filed on May 23, 2014.

(51) Int. Cl.
  *A61F 2/76* (2006.01)
  *A61F 2/70* (2006.01)
  *G01M 99/00* (2011.01)

(52) U.S. Cl.
  CPC .................. *A61F 2/76* (2013.01); *A61F 2/70* (2013.01); *G01M 99/007* (2013.01); *G01M 99/008* (2013.01); *A61F 2002/7635* (2013.01); *A61F 2002/7695* (2013.01)

(58) Field of Classification Search
  CPC ....... A61F 2002/502; A61F 2002/7695; G01B 23/32; G01M 99/007
  See application file for complete search history.

(56) References Cited

U.S. PATENT DOCUMENTS

| | | | |
|---|---|---|---|
| 4,096,733 A | 6/1978 | Cohen | |
| 4,432,223 A | 2/1984 | Paquette et al. | |
| 5,014,719 A | 5/1991 | McLeod | |
| 5,127,420 A | 7/1992 | Horvath | |
| 5,476,441 A | 12/1995 | Durfee et al. | |
| 5,623,944 A | 4/1997 | Nashner | |
| 5,911,126 A | 6/1999 | Massen | |
| 5,993,400 A * | 11/1999 | Rincoe | A61B 5/1036 600/595 |
| 6,302,918 B1 * | 10/2001 | Gramnas | A61F 2/76 623/27 |
| 6,379,393 B1 * | 4/2002 | Mavroidis | A61F 2/54 623/25 |
| 6,532,400 B1 | 3/2003 | Jacobs | |
| 6,689,075 B2 | 2/2004 | West | |

(Continued)

FOREIGN PATENT DOCUMENTS

| | | |
|---|---|---|
| CN | 201260709 Y | 6/2009 |
| CN | 102119877 B | 11/2012 |

(Continued)

*Primary Examiner* — Tran M. Tran
(74) *Attorney, Agent, or Firm* — KOS IP Law LLP

(57) ABSTRACT

A prosthetic limb test fixture is configured to mimic a human stride. An electronic management system can control the test fixture to follow the position and pattern of a particular selected gait cycle during testing. A proposed prosthesis can be attached to the test fixture. Sensor data collected during testing can be evaluated to determine whether the proposed prosthesis is likely to appropriately fit an amputee patient. Iterative adjustments may be made to the prosthesis based on test data in order to maximize the likelihood of a good fit.

8 Claims, 17 Drawing Sheets

(56) References Cited

U.S. PATENT DOCUMENTS

| | | |
|---|---|---|
| 6,755,870 B1 | 6/2004 | Biedermann et al. |
| 6,821,233 B1 | 11/2004 | Colombo et al. |
| 6,834,436 B2* | 12/2004 | Townsend ............ A61B 5/1116 33/341 |
| 6,895,830 B2* | 5/2005 | Kochersberger .... G01M 13/022 340/679 |
| 7,041,069 B2 | 5/2006 | West |
| 7,125,388 B1 | 10/2006 | Reinkensmeyer et al. |
| 7,150,762 B2 | 12/2006 | Caspers |
| 7,292,151 B2 | 11/2007 | Ferguson et al. |
| 7,383,738 B2* | 6/2008 | Schulz ................. A61F 2/468 73/781 |
| 7,581,454 B2* | 9/2009 | Clausen ................ A61F 2/76 73/862.046 |
| 7,597,017 B2 | 10/2009 | Bedard et al. |
| 7,603,911 B2* | 10/2009 | Zubok ................. A61F 2/468 73/804 |
| 7,717,962 B2* | 5/2010 | Wilson .................. A61F 2/76 623/24 |
| 7,823,460 B2* | 11/2010 | White .................. A61F 2/468 73/804 |
| 7,891,258 B2 | 2/2011 | Clausen et al. |
| 7,895,899 B2* | 3/2011 | Kelly .................... G01N 3/24 73/760 |
| 7,913,573 B2* | 3/2011 | Schulz ................. G01N 3/32 73/856 |
| 8,048,007 B2 | 11/2011 | Roy |
| 8,083,807 B2 | 12/2011 | Auberger et al. |
| 8,108,190 B2* | 1/2012 | Riener ................. G09B 23/32 703/11 |
| 8,147,436 B2 | 4/2012 | Agrawal et al. |
| 8,215,186 B2 | 7/2012 | Macomber et al. |
| 8,251,928 B2 | 8/2012 | Pusch |
| 8,311,671 B2* | 11/2012 | Tokita ................. A61H 1/0237 700/245 |
| 8,388,351 B2* | 3/2013 | Potti Cuervo ......... G09B 23/32 434/274 |
| 8,403,997 B2 | 3/2013 | Sykes et al. |
| 8,419,437 B2 | 4/2013 | Wesp et al. |
| 8,452,458 B2 | 5/2013 | Even-Zohar |
| 8,551,026 B2 | 10/2013 | Alwan et al. |
| 8,655,808 B2* | 2/2014 | Palmer .................. A61B 5/1114 706/12 |
| 8,808,214 B2 | 8/2014 | Herr et al. |
| 8,828,093 B1 | 9/2014 | Kuiken et al. |
| 8,858,648 B2 | 10/2014 | De Roy |
| 8,869,626 B2* | 10/2014 | Clausen ................ A61F 2/76 73/812 |
| 9,060,884 B2* | 6/2015 | Langlois ............... A61F 2/70 |
| 9,072,463 B2 | 7/2015 | Sanders et al. |
| 9,221,177 B2* | 12/2015 | Herr ..................... B25J 9/1694 |
| 9,232,911 B2 | 1/2016 | Wilson et al. |
| 9,351,857 B2 | 5/2016 | Carignan et al. |
| 9,357,947 B2 | 6/2016 | Degree et al. |
| 9,378,662 B2* | 6/2016 | Carroll .................. G09B 23/30 |
| 9,443,203 B2 | 9/2016 | Young et al. |
| 9,492,709 B2 | 11/2016 | Dilli et al. |
| 9,498,401 B2 | 11/2016 | Herr et al. |
| 9,603,724 B2 | 3/2017 | Geyer et al. |
| 9,693,883 B2* | 7/2017 | Herr .......................... A61F 2/68 |
| 9,737,419 B2 | 8/2017 | Herr et al. |
| 9,993,181 B2 | 6/2018 | Ross |
| 10,307,272 B2* | 6/2019 | Herr ..................... A61F 5/0127 |
| 10,406,059 B2* | 9/2019 | Agrawal ............... A61H 1/0262 |
| 10,478,121 B2* | 11/2019 | Pusch ................... A61B 5/1122 |
| 10,813,591 B2* | 10/2020 | Branch ................. A61B 5/1127 |
| 10,898,350 B2* | 1/2021 | Hippensteal .............. A61F 2/70 |
| 2002/0052663 A1 | 5/2002 | Herr et al. |
| 2004/0039454 A1 | 2/2004 | Herr et al. |
| 2005/0278157 A1* | 12/2005 | Raschke ................ G06T 13/40 703/6 |
| 2007/0171199 A1* | 7/2007 | Gosselin ................ G06F 3/016 345/156 |
| 2007/0255424 A1* | 11/2007 | Leydet ................... A61F 2/76 600/595 |
| 2008/0281550 A1 | 11/2008 | Hogle et al. |
| 2010/0152629 A1* | 6/2010 | Haas, Jr. ............. A63B 21/4011 601/34 |
| 2013/0024006 A1 | 1/2013 | Balli et al. |
| 2013/0110011 A1 | 5/2013 | McGregor et al. |
| 2013/0144402 A1 | 6/2013 | Clausen et al. |
| 2013/0310949 A1 | 11/2013 | Goldfarb et al. |
| 2014/0094717 A1 | 4/2014 | Wilson et al. |
| 2014/0343460 A1 | 11/2014 | Evans, III et al. |
| 2015/0051710 A1 | 2/2015 | Herr et al. |
| 2015/0066156 A1 | 3/2015 | Geyer et al. |
| 2015/0099253 A1 | 4/2015 | De Roy |
| 2015/0100292 A1 | 4/2015 | Macomber et al. |
| 2015/0127117 A1 | 5/2015 | Herr et al. |
| 2015/0164661 A1 | 6/2015 | Ragnarsdottir et al. |
| 2015/0182354 A1 | 7/2015 | Bonnet et al. |
| 2015/0209159 A1 | 7/2015 | Goldfarb et al. |
| 2016/0074180 A1* | 3/2016 | Lenzi ................... A61F 2/6607 623/24 |
| 2016/0175120 A1* | 6/2016 | Klaene ................... A61F 2/76 623/33 |
| 2016/0206447 A1 | 7/2016 | Auberger et al. |
| 2017/0143250 A1* | 5/2017 | Branch ................. A61B 5/6884 |
| 2020/0315818 A1* | 10/2020 | Irrinki ..................... A61F 2/72 |

FOREIGN PATENT DOCUMENTS

| | | |
|---|---|---|
| CN | 203154010 U | 8/2013 |
| KR | 101272249 B1 | 5/2013 |

\* cited by examiner

PROSTHETIC LIMB FITTING APPARATUS FOR PREDICTING THE EFFECT OF A PROPOSED PROSTHETIC LIMB ON ABLE JOINTS

CROSS-REFERENCE TO RELATED APPLICATIONS

The application is a continuation of U.S. application Ser. No. 14/721,169, filed May 26, 2015, which claims the benefit of U.S. Provisional Application No. 62/002,722, which was filed May 23, 2014, the entireties of which are hereby incorporated by references.

BACKGROUND

The present disclosure relates to the field of therapy for correcting or improving a human stride, and more particularly to correctly fitting prosthetic limbs or braces.

As simple and typical as it may seem, walking is actually a complex motion involving multiple joints. As a person completes one complete stride, from one heel strike to the next heel strike on the same foot, the person's hips, knee, ankle and toe joints move through various planes and angles. Also, each person walks in a manner that is unique to them. A person's gait cycle is a measurement that quantifies such motion during a person's typical stride. Although there are average patterns in gait cycles, each person has a unique gait cycle.

Many people have flawed or irregular gait cycles. Biomechanical abnormalities can be caused by flaws in a person's gait cycle. Sometimes a person's gait cycle can be evaluated and corrected by treatment in order to correct or relieve such abnormalities.

Patients who have had lower limbs amputated or substantial injuries typically experience major alterations in their gait cycles. Many patients will alter their striding motion to compensate for their disability. This modified gait can potentially cause stress and long term damage to other areas of the body.

For amputees, in particular, the process of fitting a prosthesis often relies heavily on the judgment of the technician performing the fitting. Although such technicians can develop substantial skill with experience, they still must substantially rely on subjective judgment rather than empirical data. As such, optimizing the fit of a prosthesis, and particularly a lower-limb prosthesis, can be time-consuming and inexact.

SUMMARY

Accordingly, there is a need in the art for a system and method that can provide empirical data to assist in correctly fitting prostheses and/or braces with unique patients. There is also a need in the art for a method of using such empirical data in the selection and fitting of a prosthesis. There is a further need in the art for a system and method that can provide empirical data to assist in devising treatment programs for patients having flawed gait cycles.

In accordance with one embodiment, the present disclosure provides a prosthesis fitting apparatus. A test fixture comprises a hip module and a knee module, the hip module being connected to the knee module by an elongate thigh pylon, the knee module being releasably attachable to a prosthesis. An electronic controller has access to a desired gait cycle data, the gait cycle data comprising a dataset of positions of components of a human lower limb during a complete stride. The hip module comprises a hip joint configured to mimic movement of a human hip, the hip module comprising one or more hip motors connected to the electronic controller and configured to move the hip joint in a manner directed by the electronic controller. The knee module comprises a knee joint configured to mimic movement of a human knee, the knee module comprising one or more knee motors connected to the electronic controller and configured to move the knee joint in a manner directed by the electronic controller. The test fixture is configured to complete a stride in a manner directed by the electronic controller. The electronic controller is configured to direct the hip and knee motors to mimic the desired gait cycle data when the prosthesis is attached. A plurality of force sensors are configured to measure forces exerted at one or more of the hip and knee modules when the test fixture completes a stride as directed by the electronic controller, and to communicate measured force data to the electronic controller.

In one such embodiment, the knee module is releasably attachable to a proximal end of an elongate shin pylon, and a distal end of the elongate shin pylon is releasably attachable to a foot prosthesis. Another embodiment additionally comprises a foot module comprising an ankle joint. The foot module is configured so that the ankle joint mimics the movement of a human ankle, and the distal end of the elongate shin pylon is releasably attachable to the foot module.

In another embodiment, a length of one or more of the thigh and knee pylons can be adjusted.

In yet another embodiment, the test fixture is configured to mimic a patient weight associated with the desired gait cycle.

In accordance with another embodiment, the present disclosure provides a method of fitting a lower-limb prosthesis to a patient. The method includes receiving and electronically storing a set of patient parameters including a patient weight and a patient height, and also receiving and electronically storing a test gait cycle. The test gait cycle comprises kinematic and position data regarding one or more joints of a patient's lower limb during a test walking stride. The method includes operating a test fixture through the test walking stride while a lower-limb prosthesis is mounted on the test fixture. Operating the test fixture through the test walking stride comprises directing the test fixture to apply the patient parameters and to move in accordance with the test gait cycle. The method further includes receiving force sensor data regarding the measured forces at one or more joints of the test fixture. The force sensor data comprising forces measured at the one or more joints while the test fixture is operated through the walking stride of the patient. The method still further includes comparing the force sensor data to desired force parameters.

In another embodiment, if the force sensor data exceeds one or more of the desired force parameters additionally comprising making an adjustment to the prosthesis and again operating the test fixture through the test walking stride.

In yet another embodiment, the test walking stride simulates a desired gait cycle of a patient.

Still another embodiment additionally comprises iteratively adjusting the prosthesis and again operating the test fixture through the test walking stride until the force sensor data is within a defined desirable range of a desired force parameter.

In some embodiments, the desired gait cycle of the patient comprises a healthy gait cycle of an amputee patient. The desired gait cycle can reflect a gait cycle measurement taken when the amputee patient was whole.

Yet another embodiment additionally comprises measuring an amputee patient's gait cycle of the amputee patient's whole leg.

In a further embodiment the desired gait cycle is taken from a database of average human gait cycles.

A still further embodiment additionally comprises receiving angular position sensor data regarding measured angles at one or more locations on the prosthesis. The angular position data comprises angular positions measured at the one or more locations on the prosthesis.

DESCRIPTION

Gait analysis is the study of human motion by using instrumentation and human observation. Gait analysis involves tracking and analysis of movement and forces during a single sequence of functions of one lower limb, known as the gait cycle. When analyzing gait movements, the stride of the limb is evaluated. A stride is defined as the linear distance between corresponding heel strikes of the same foot, in the movements taken by the lower limb while walking through that linear distance. A stride is comprised of two components: the stance phase, and the swing phase.

Figure 1:
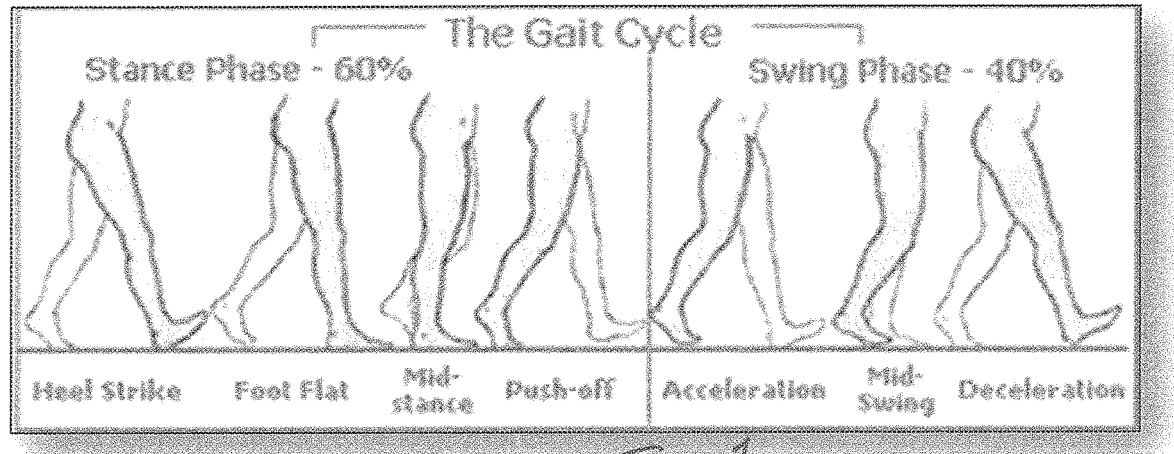
FIG. 1 is a diagram depicting a human gait cycle.

With reference to FIG. 1, the stance phase is the first portion of a stride, and the swinging phase is the second.

With continued reference to FIG. 1, the stance phase comprises four subdivided categories. The first category is the initial contact sub-phase, which is the instance that the heel strikes the ground. The second is the loading response sub-phase, which includes a flat foot position and the time period instantly following the lift of the opposite extremity off the ground. Weight shift occurs during this time. The third part of the stance sub-phase is the mid-stance and includes the time interval from when the opposite extremity leaves the ground until the ankles of both legs align when being viewed from the side plane. The fourth part of the stance sub-phase is the push off. This is the time interval from when the ankles of both legs are aligned to the time just prior to initial ground contact of the swinging leg. This symbolizes the time interval from initial contact of the swinging leg to just before the other leg reaches the ground.

Continuing with reference to FIG. 1, the swinging phase of a human stride in the context of gait analysis comprises three sub-phases. The first sub-phase is the initial swing, which is the lifting of the leg from the ground to the position of maximum knee flexion. The second sub-phase is the mid swing, which involves the swinging of the leg immediately following the knee flexing until the tibia of the leg is in a vertical position. The third and final sub-phase of the swing phase is the terminal swing which is the motion following when the tibia is in a vertical position until just before the heel comes in contact with the ground completing one stride.

Figure 2:
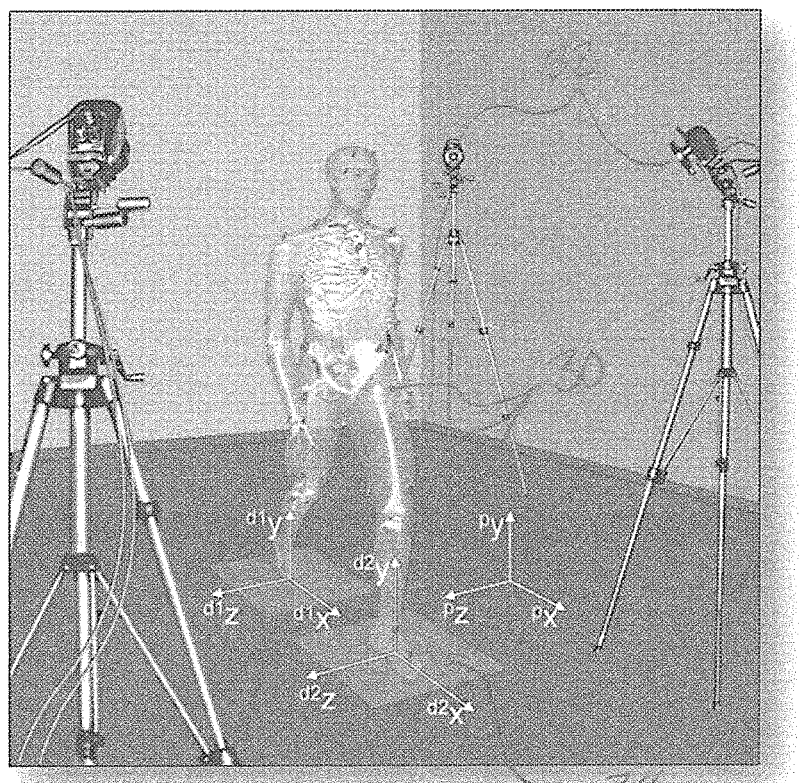
FIG. 2 is a schematic perspective view depicting a system for obtaining gait cycle data.

By analyzing a patient's gait, doctors are able to identify causes for issues the patient may be experiencing and work to find corrective solutions to potential problems. With reference next to FIG. 2, a patient's gait can be recorded and analyzed by attaching reflective markers 30 in several strategic locations to the patient. A test is then conducted in a lab equipped with cameras 32 and sensors, including force-measuring sensors built into floor panels 34, to capture movement and force data. During the test, the patient will walk, preferably taking at least one and potentially a plurality of complete strides. The cameras 32 and sensors are linked to a computer, which receives data from the cameras and sensors, electronically stores the data, and uses software to analyze the data and, in some instances, create a 3D digital model of the patient and the respective motion.

Figure 3:
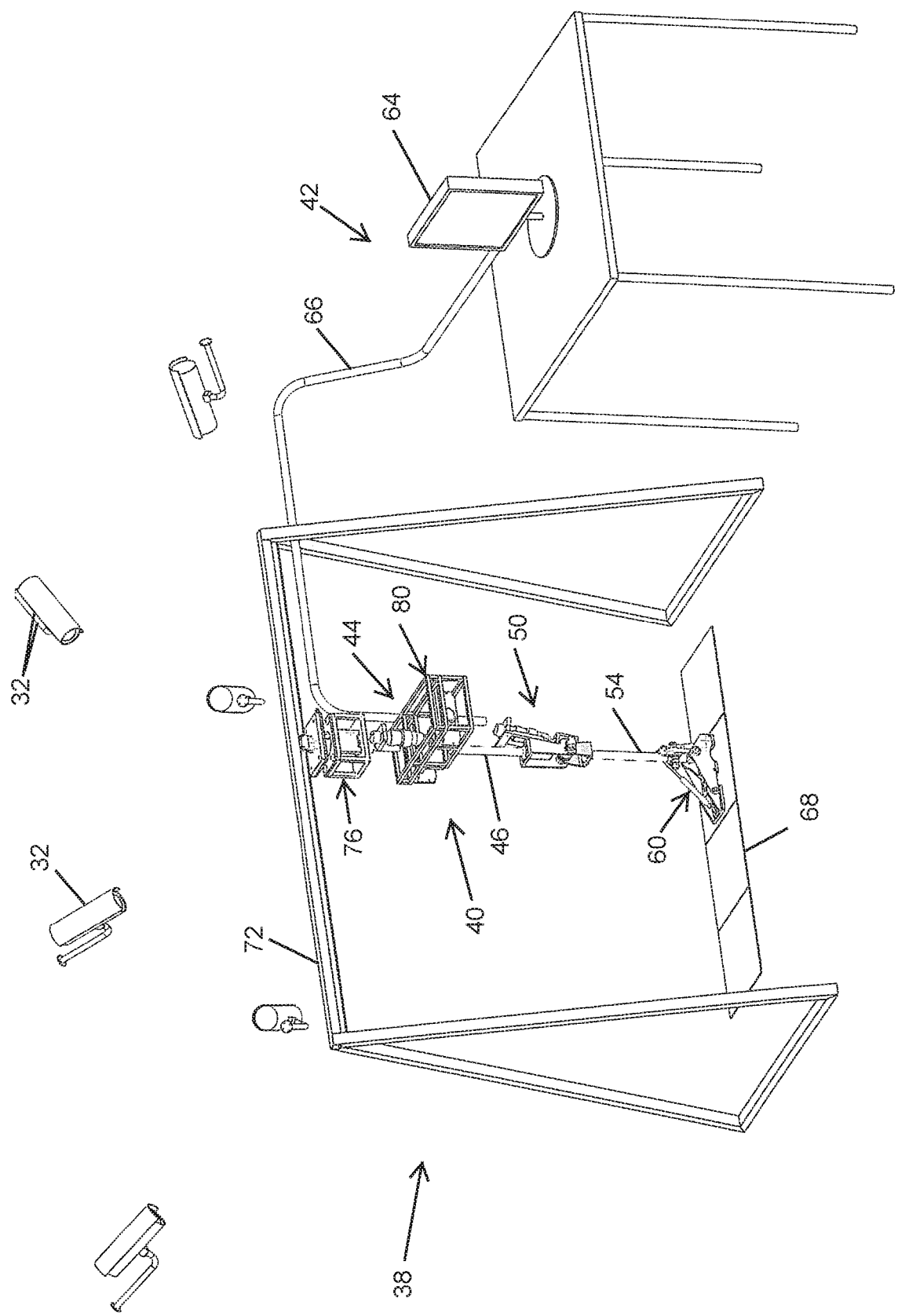
FIG. 3 is a perspective view of a prosthesis testing system in accordance with one embodiment.
Figure 4:
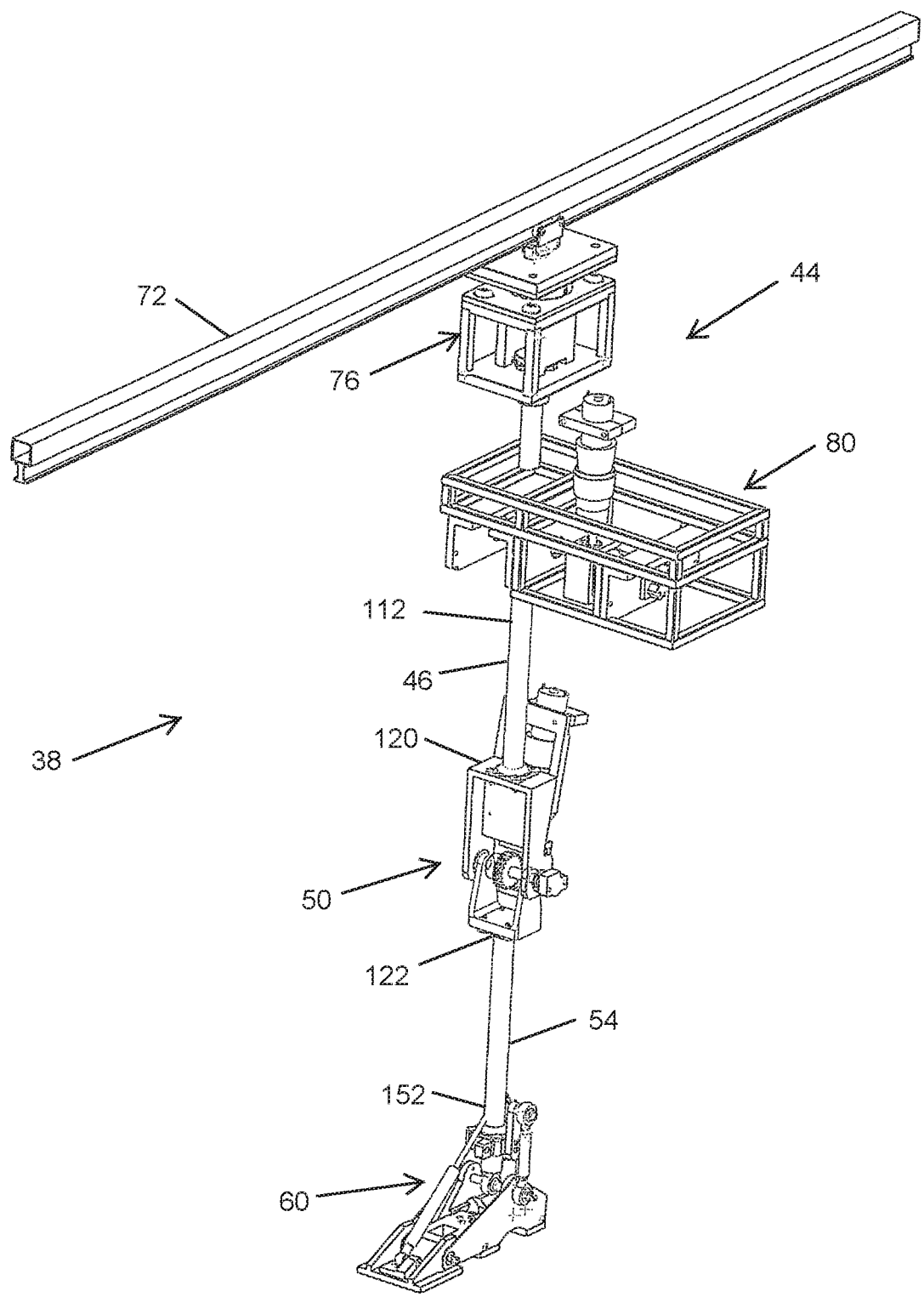
FIG. 4 is another view of the test fixture of FIG. 3.

With reference next to FIG. 3, an embodiment of a system 38 for testing a lower-limb prosthesis is shown. With reference also to FIG. 4, the system comprises a test fixture 40, or robot leg, and an electronic management system 42.

With continued reference to FIGS. 3 and 4, the test fixture 40 is configured to "walk" for one complete stride from one heel strike to the next heel strike on the same foot while mimicking the movement of a patient's actual lower limb during that stride. The illustrated test fixture 40 is self-supporting during the process of making the stride. Preferably, the test fixture 40 includes structure that mimics each of the structures of a human leg. More specifically, the test fixture 40 includes a pelvic section 44 configured to mimic the movement of a patient's pelvis, including the patient's hip. An elongate thigh section or thigh pylon 46 connects the pelvic section 44 to a knee module 50 which includes a knee joint 52 configured to mimic the movement of a natural human knee joint 52. The knee module 50 is connected via an elongate shin section, or shin pylon 54, to a foot module 60, which includes an ankle joint 62, and which is configured to mimic the movement of the foot and ankle of a patient. Preferably each of the modules, and joints within the modules, are configured to be able to rotate in each of the x, y, and z axes in order to be capable of replicating a particular patient's gait cycle through a complete stride.

Preferably, the test fixture 40 is proportioned in accordance with average anthropometric data, such as the proportion of the length of the thigh pylon 46 relative to the length of the shin pylon 54 being consistent with typical human leg proportions. In some embodiments, the lengths of the thigh and shin sections can be adjusted so as to match measured data taken from a particular patient. Similarly, in some embodiments the length of the foot module 60 can be modified to match measured data taken from a particular patient.

Preferably, a plurality of sensors are arranged on the test fixture 40. Such sensors can include reflective markers 30 so that the actual motion of various parts of the test fixture 40 can be tracked; angle measurement sensors, which can track angular movement of each joint, preferably in each of the x, y and z axes, during the test; and force sensors configured to measure forces in several different directions, including shear forces, in each of the joints and elsewhere throughout the test fixture 40.

With particular reference again to FIG. 3, the electronic management system comprises a computer system 64 having software for data acquisition and analysis, as well as for controlling operation of the test fixture 40. A data acquisition system of the electronic management system acquires data generated by the test fixture 40 during a test. For example, a wire 66 from the test fixture 40 delivers data generated by the various sensors to the electronic management system 42. The wire 66 also communicate instructions from the electronic management system 42 to the test fixture 40. Of course, it is contemplated that other communication means, such as Wi-Fi or other wireless communication, can be employed between the electronic management system 42 and the test fixture 40 or any data acquisition structure that may be employed.

In the illustrated embodiment, the electronic management system 42 comprises several cameras that track movement of the test fixture 40, such as by tracking movement of reflective markers 30, and relay data regarding such movement to the electronic management system 42. Similarly, in the illustrated embodiment, a test floor 68 comprises several pressure sensing plates and/or pressure sensors disposed at a particular locations along the test route. The sensors detect pressure resulting from contact of the test fixture 40 with the floor, including the location of such contact, and relay such information to the electronic management system 42.

Figure 5:
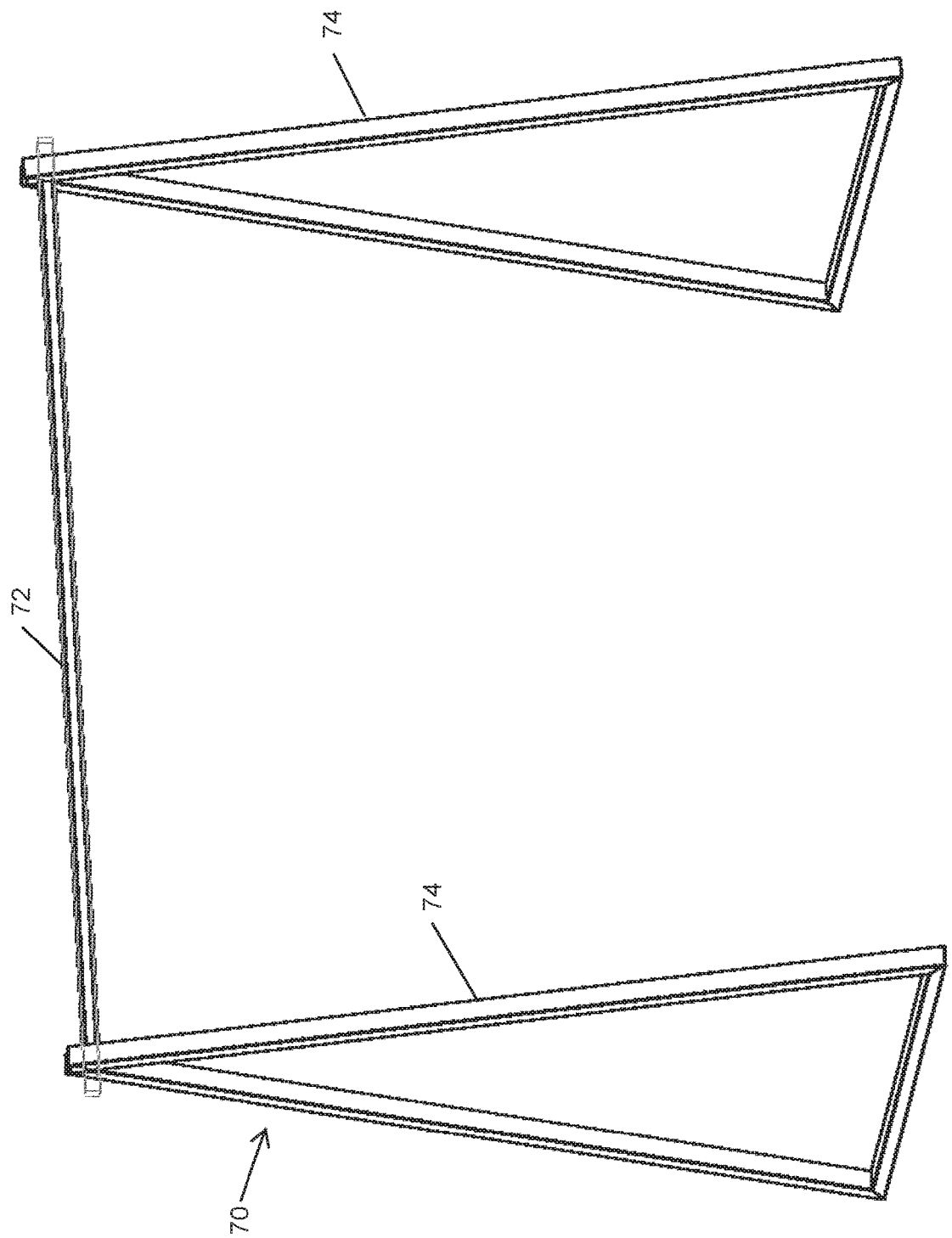
FIG. 5 depicts a track portion of the test fixture of FIG. 3.

With reference next to FIG. 5, an embodiment of a track system 70 is illustrated. The illustrated track system 70 comprises an elongate track 72 having supports 74 disposed at each end. The track 72 is configured to support the test fixture 40 during operation. More specifically, in the illustrated embodiment the track system 70 remains stationary while the test fixture 40 moves during test operation. The elongate track preferably is sufficiently long to accommodate a full stride of the test fixture 40, which in one embodiment is about six feet. In the illustrated embodiment, the track comprises an I-beam, and thus provides a secure support for the test fixture 40.

Figure 6:
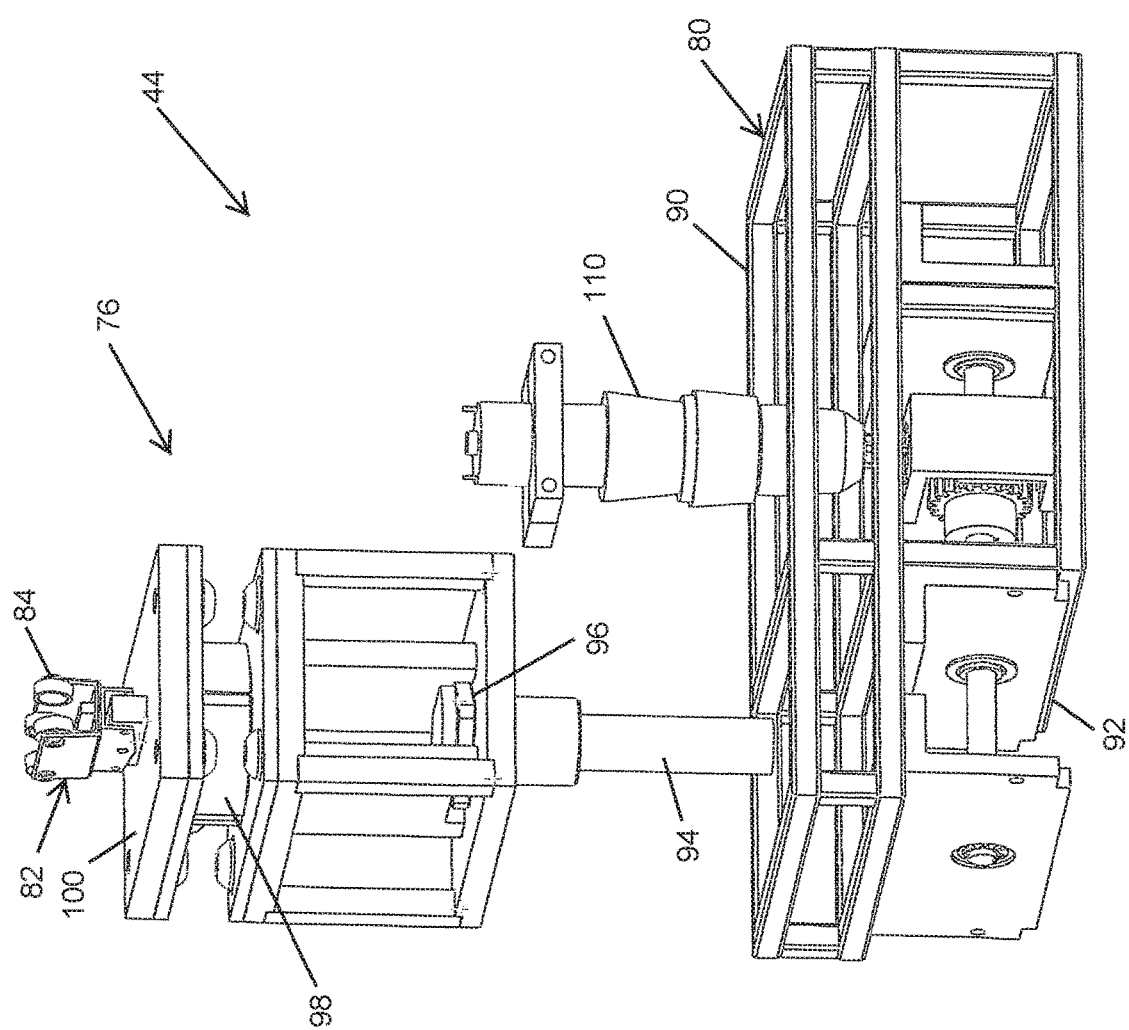
FIG. 6 is a perspective view of a track interface module and hip module in accordance with the embodiment of FIG. 3.
Figure 6A:
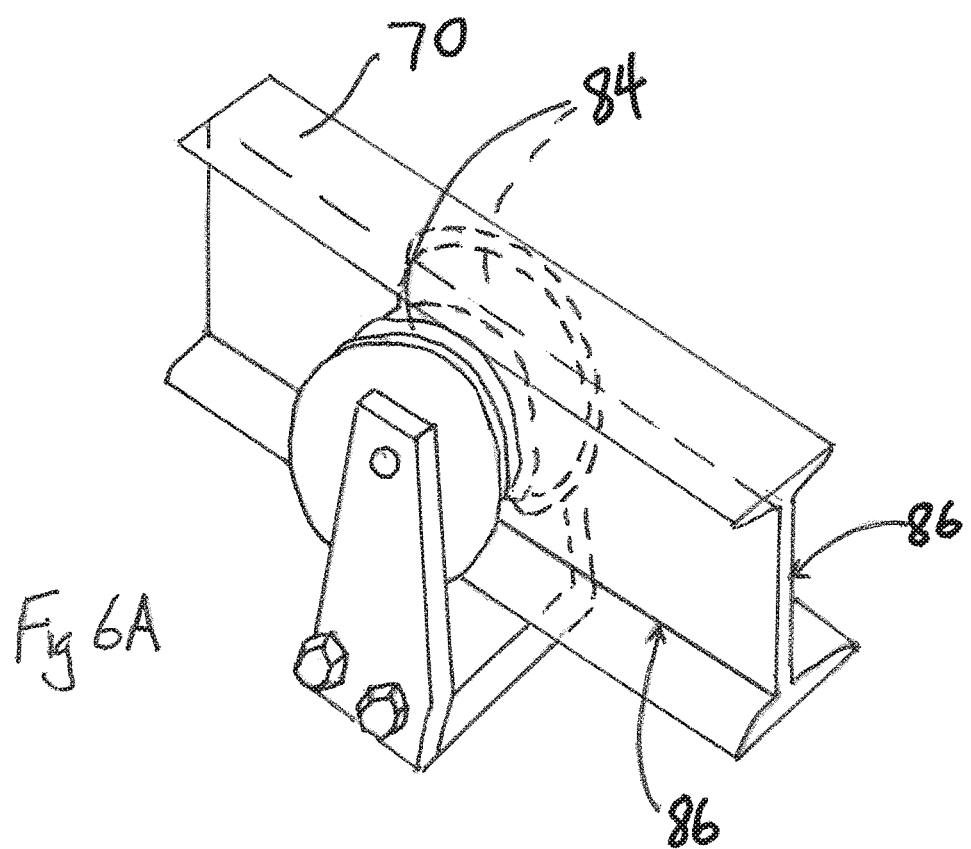
FIG. 6A is a close-up perspective view of wheels of the embodiment of FIG. 6 engaged with a track of the embodiment of FIG. 5.
Figure 7:
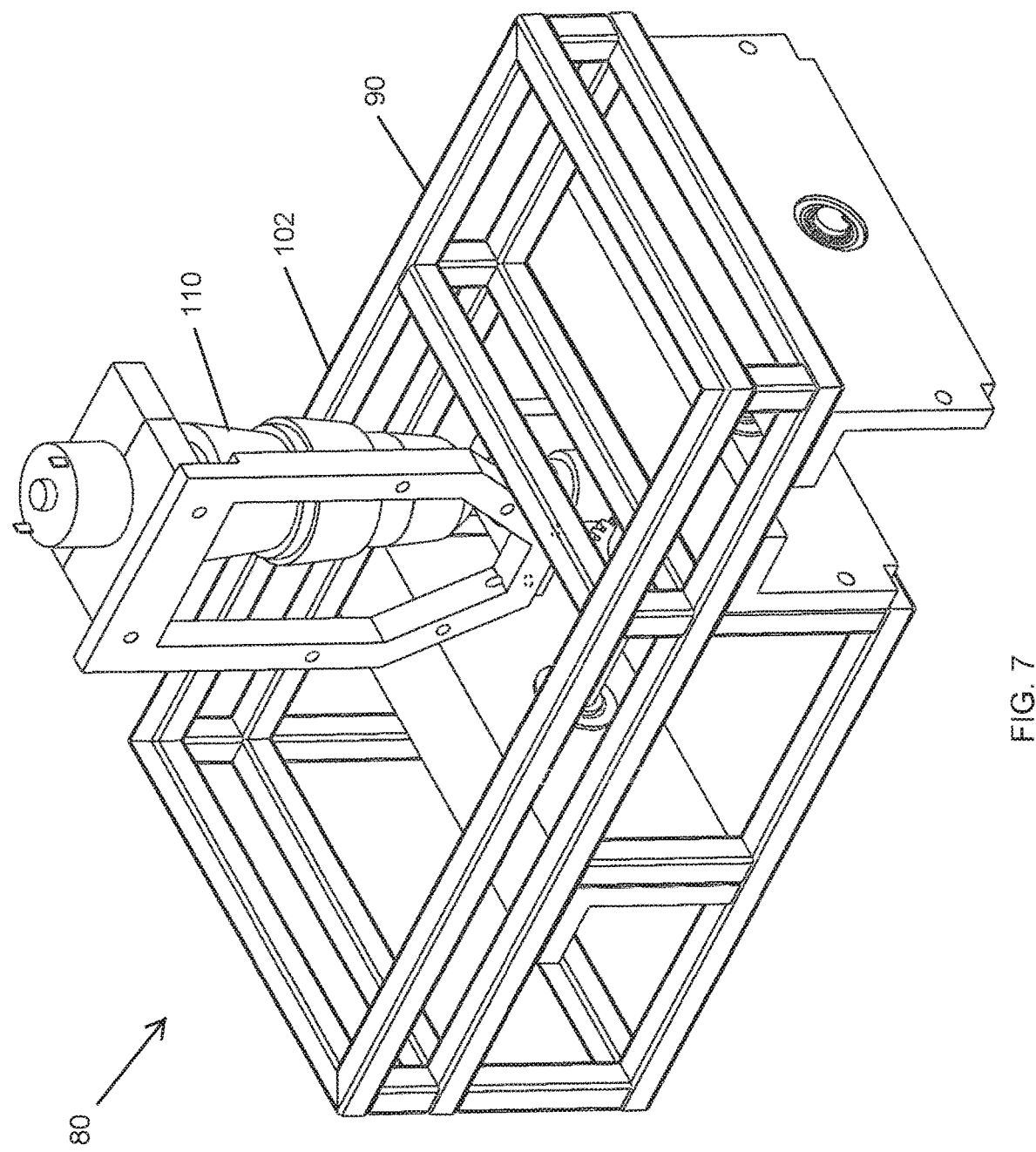
FIG. 7 is another perspective view of a hip module in accordance with the embodiment of FIG. 3.
Figure 9:
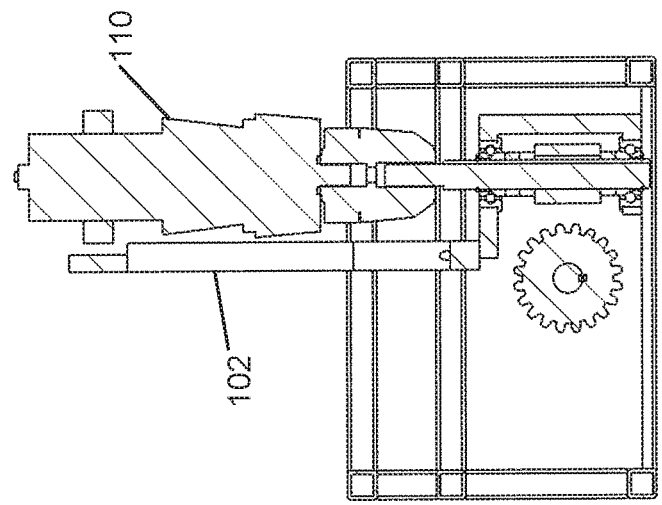
FIG. 9 is a cross section view of the hip module of FIG. 8 taken along lines 9-9.
Figure 8:
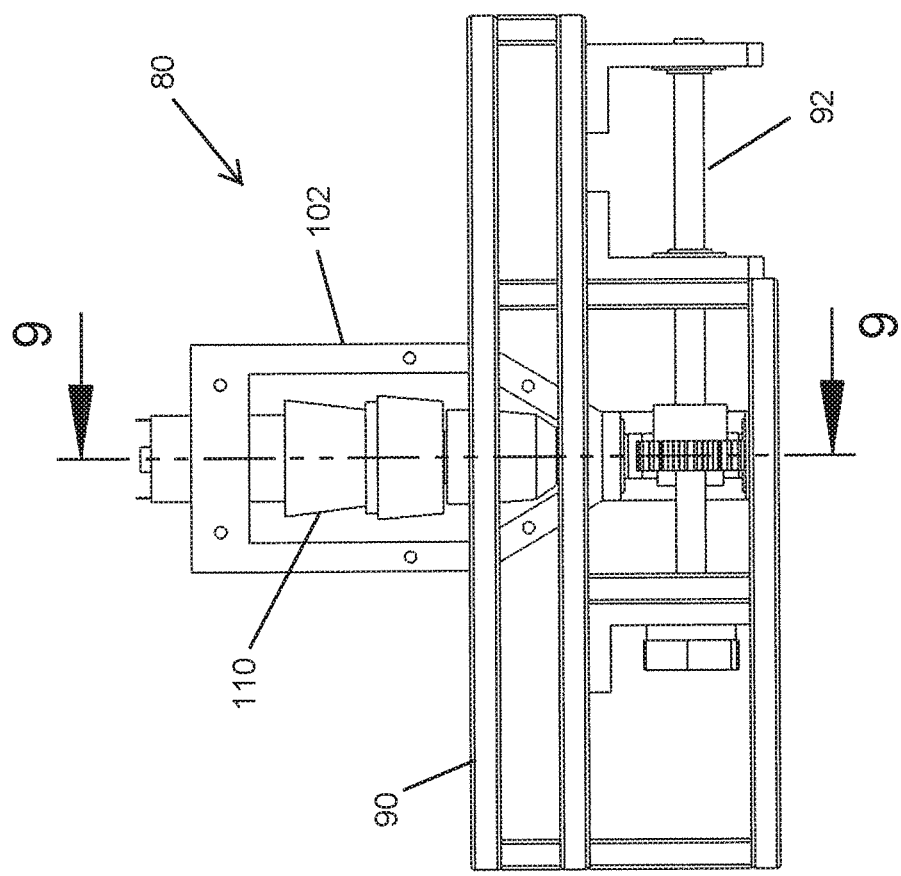
FIG. 8 is a side view of the hip module of FIG. 7.

With reference next to FIG. 6, an embodiment of the pelvis section 44 of the test fixture 40 is illustrated. The pelvis section 44 comprises an interface module 76 and a hip module 80. The interface module 76 includes a connector 82 that is adapted to connect to the track 72. With additional reference to FIG. 6a, in the illustrated embodiment the connector 82 includes a plurality of wheels 84 that are configured to fit within C-shaped channels 86 formed on opposing sides of the track 72 I-beam. As such, the connector 82 rolls along the track 72, but does not rotate about the axis of the track 72. Preferably the I-beam is configured so that there is a substantially close fit between the upper and lower portions of the C-shaped channels 86 and the wheels 84 of the connector 82. As such, the track 72 can provide both upwardly-directed forces to support the test fixture 40 and downwardly-directed forces to press down upon the test fixture 40 to simulate a human's weight.

It is to be understood that various other structures can be employed for connecting the test fixture 40 to the track 72, and other embodiments of structures can be used for the track 72. For example, in another embodiment the connector 82 of the interface module 76 may comprise a linear bearing 96, and the track 72 can be shaped to specifically fit the linear bearing 96. Furthermore, preferably the connection between the connector 82 and track 72 is such that it will allow linear movement along the length of the track 72 but the connector 82 will not substantially rotate about the axis of the track 72. Instead, preferably such movement is controlled by and through the test fixture 40.

It is to be understood that the illustrated track system 70, and the manner in which it connects to the test fixture 40, can vary in other embodiments. For example, in another embodiment, the support system may be substantially rigidly attached to the test fixture 40, and the support system can be configured to move linearly during operation of the test fixture 40 through a stride. In one such embodiment, the support system rolls upon a plurality of wheels which may, in some embodiments, be confined to a track 72. In another embodiment, the support system may be supported by and directed by one or more linear bearings.

With reference next to FIGS. 6-9, the hip module 80 comprises a frame-like hip box 90 that supports a horizontal rotating shaft 92. A pin 94 of the interface module 76 can be attached to the hip box 90. The pin 94 preferably is configured to move vertically relative to a linear bearing of the interface module 76, and thus the hip box 90 can move vertically relative to the interface module 76. In the illustrated embodiment, a turntable 98 is disposed adjacent a base 100 of the connector 82 and is configured to rotate 360° about a vertical or Y axis.

The hip box 90 supports a motor support 102 which in turn supports a motor 110 such as a servo motor that is linked to the rotating shaft 92. A proximal end 112 of the elongate thigh pylon 46 preferably is attachable via a connector (not shown) to the rotating shaft 92 and is thus configured to rotate with the rotating shaft 92. As such, actuation of the hip motor 110 prompts movement of the thigh pylon 46 in accordance with the human stride. In additional embodiments other structures may be employed, including one or more additional servo motors. For example, in one embodiment a motor can be applied to rotate the hip module 80 at the turntable 98. Further, a servo motor 110 can be applied to regulate forces as the hip box 90 moves vertically relative to the interface module 76. In another embodiment, an axle and associated motor can cooperate to apply and control tilt of the hip box 90.

Figure 10:
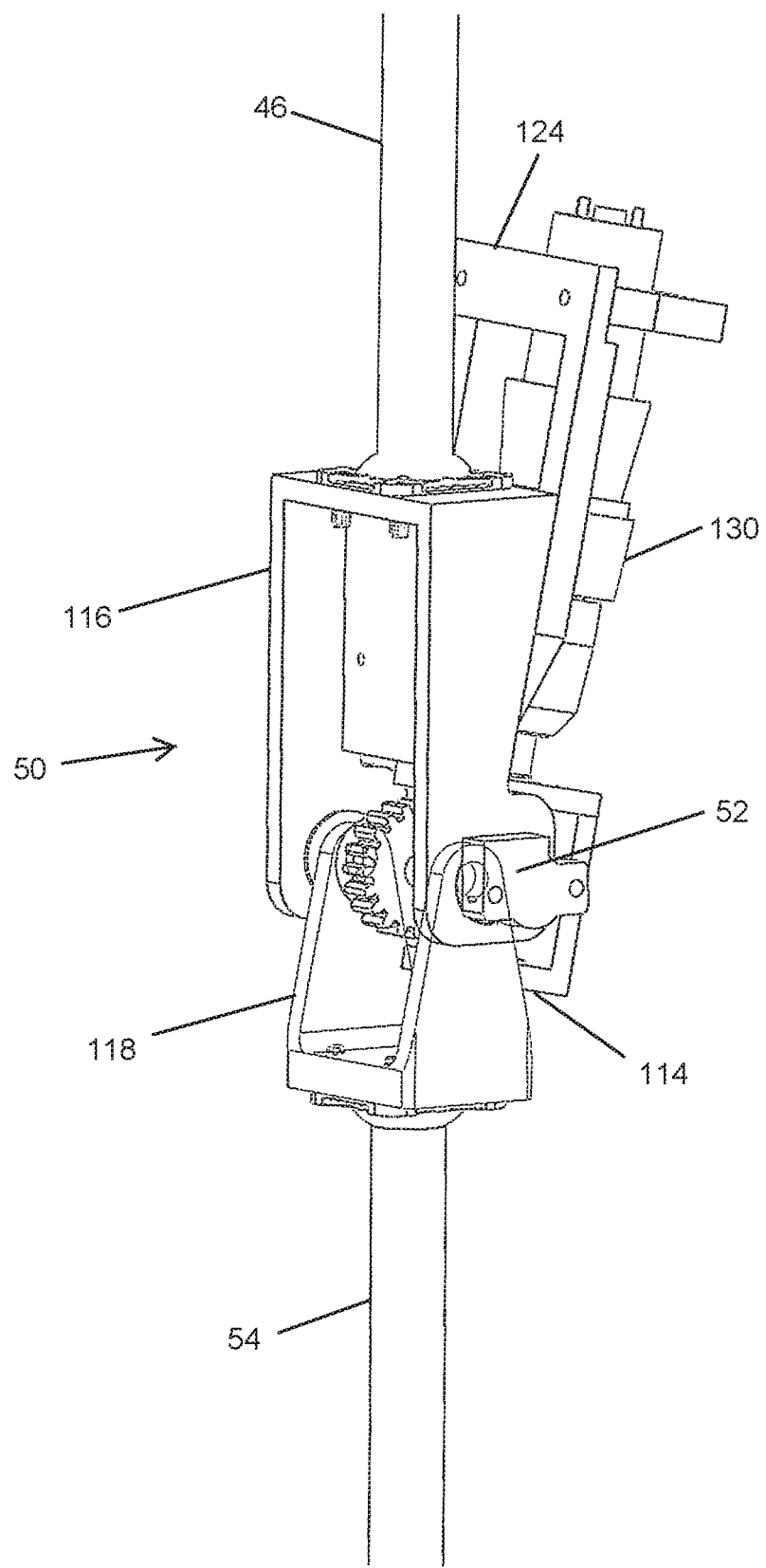
FIG. 10 is a perspective view of a knee module in accordance with the embodiment of FIG. 3.

With reference next to FIG. 10, a knee module 50 comprises a horizontal axis 114 and upper and lower mount brackets 116, 118 having connectors that attach to a distal end of the thigh pylon 46 and a proximal end 122 of the shin pylon 54, respectively. A mount bracket 124 supports a servo motor 130 that is configured to bend the knee joint 52 at the horizontal axis 114 to simulate a human knee joint 52.

Figure 11:
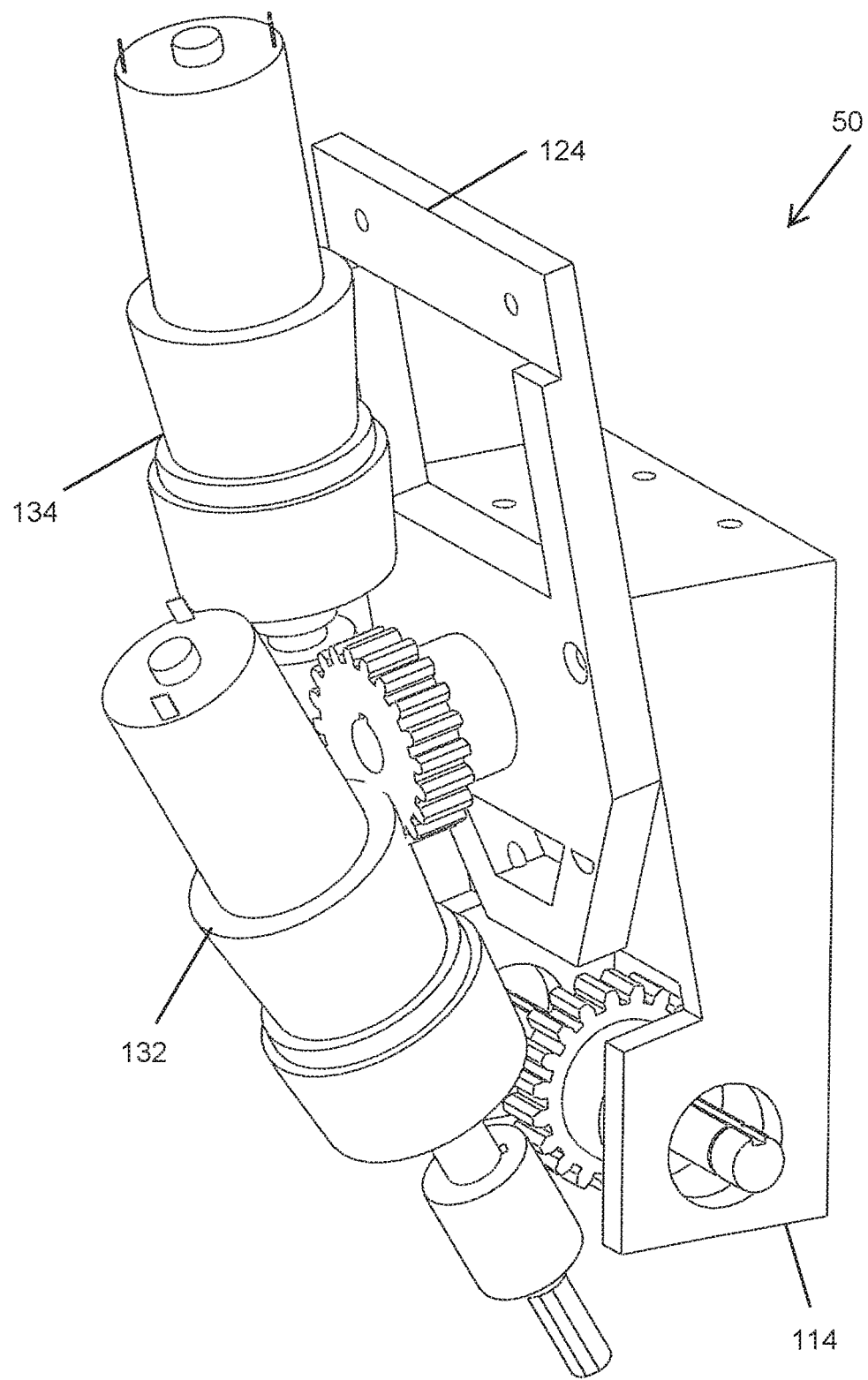
FIG. 11 is a perspective view of another embodiment of a knee module in accordance with the embodiment of FIG. 3.
Figure 13:
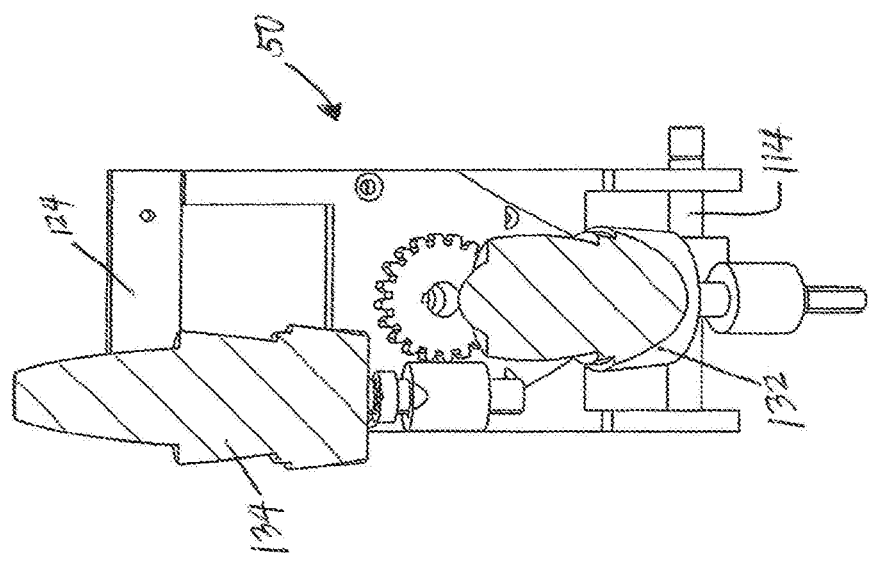
FIG. 13 is a cross section of the knee module of FIG. 12 taken along lines 13-13.
Figure 12:
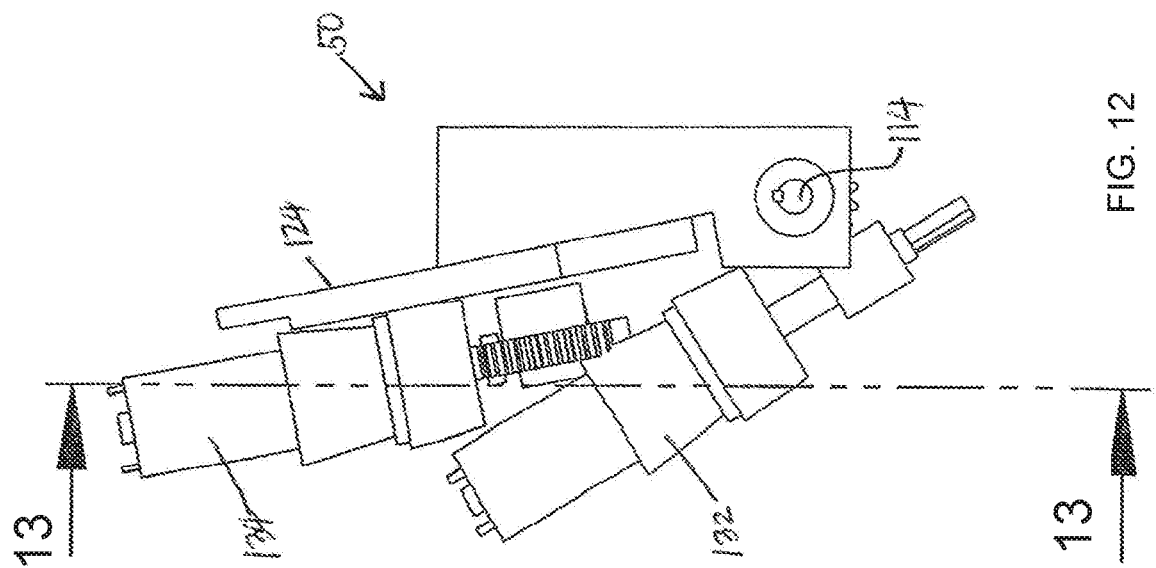
FIG. 12 is a side view of the knee module of FIG. 11.

In another embodiment, such as the embodiment illustrated in connection with FIGS. 11-13, the knee module 50 may employ first and second knee servo motors 132, 134. The first motor 132 may be attached and configured to rotate the knee about the horizontal axis 114, which is a substantially horizontal x axis. The second knee motor 134 can be configured to rotate the upper bracket 116 about a y axis parallel to the x axis. As depicted in FIG. 11, the horizontal axle 114 can be mounted so as to allow some measure of y axis rotation.

It is to be understood, of course, that other specific structures can be employed to simulate a patient's knee joint, and that other structures may employ more or less motors in order to control the knee joint to mimic, or more truly mimic, a natural human gait cycle.

Figure 14:
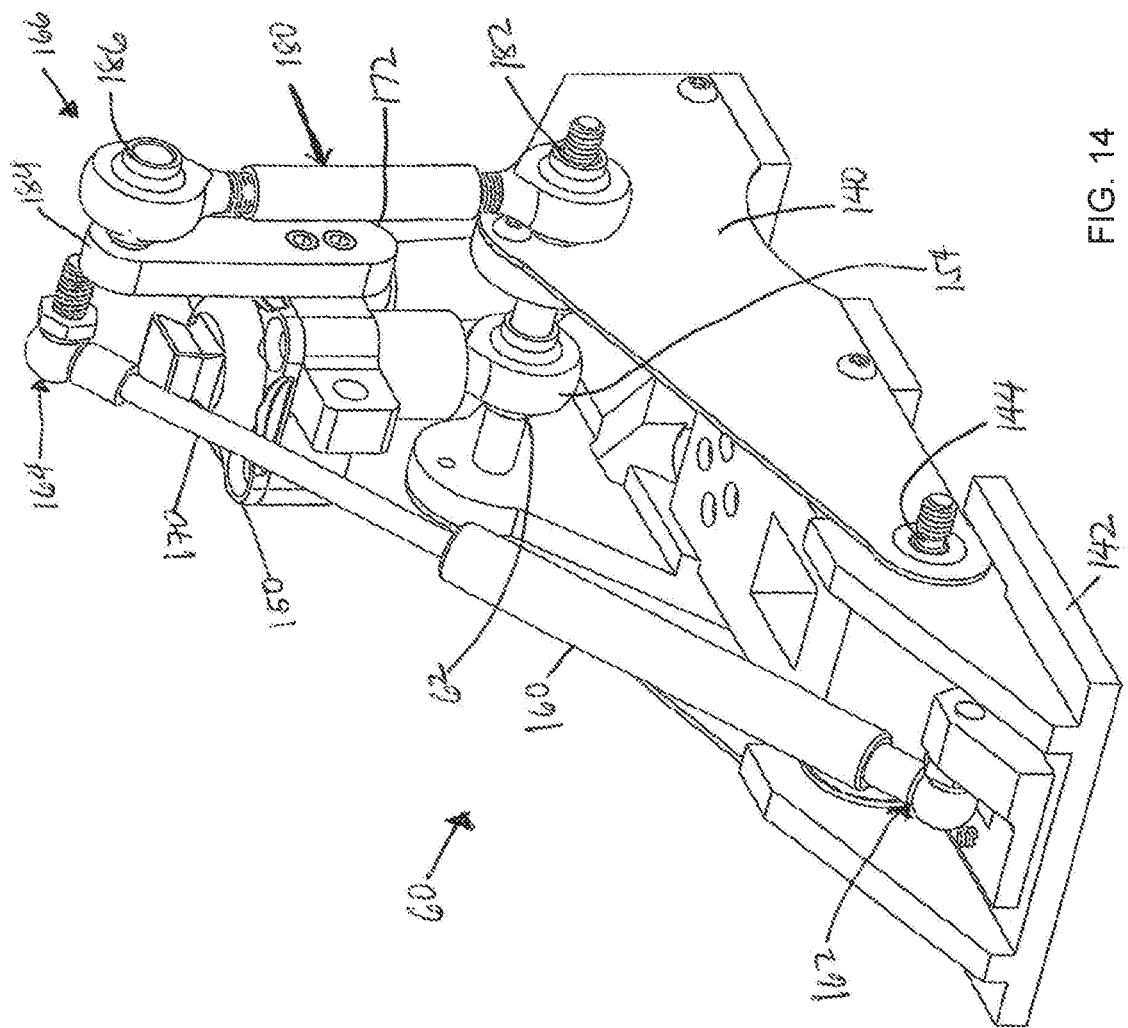
FIG. 14 is a perspective view of a foot module in accordance with the embodiment of FIG. 3.
Figure 16:
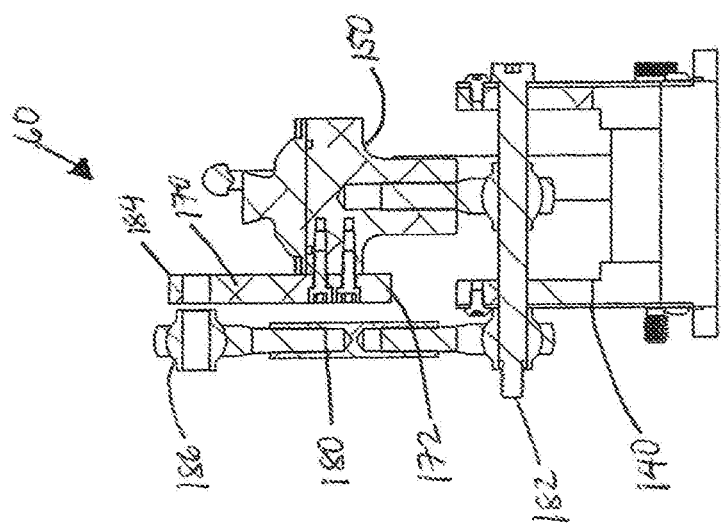
FIG. 16 is a cross sectional view taken along lines 16-16 of FIG. 15.
Figure 15:
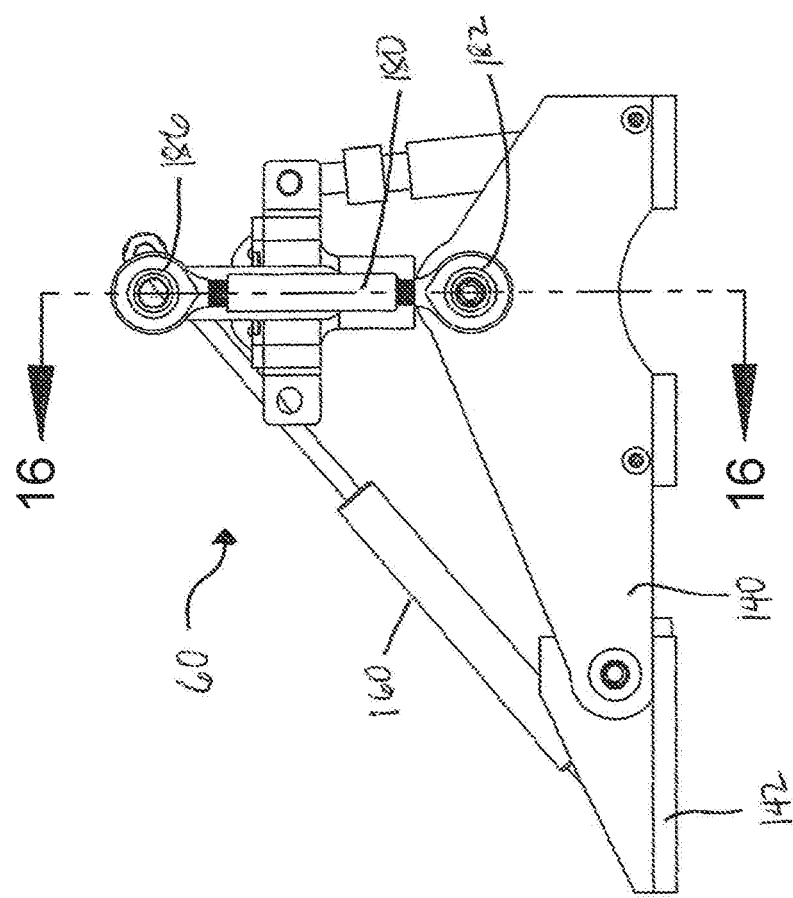
FIG. 15 is a side view of the foot module of FIG. 14.

With reference next to FIGS. 14-16, the illustrated foot module 60 comprises a foot bracket 140 configured to simulate a human foot. A toe plate 142 is attached to the foot bracket 140 at a horizontal pin 144 so that the toe plate 142 can rotate relative to the foot bracket 140. An ankle bracket 150 is configured to attach to the distal end 152 of the shin pylon 54 and further to attach to the foot bracket 140. In the illustrated embodiment, the ankle bracket 150 engages a bearing 154 supported by the foot bracket 140. The bearing 154 enables the foot bracket 140 to have a 360° range of motion relative to the ankle bracket 150, thus simulating a human ankle.

In the illustrated embodiment, a damper 160, such as a hydraulic cylinder, has a first end 162 attached to the toe plate 142 and a second end 164 attached to a damper arm assembly 166. The damper arm assembly 166 in the illustrated embodiment comprises an ankle bracket arm 170 having a first end 172 rotatably connected to the ankle bracket 150 and a foot arm 180 having a first end 182 connected to the foot plate 140. Second ends 184, 186 of the ankle bracket arm 170 and the foot arm 180 are connected to one another and are also connected to the second end 164 of the damper 160. In this manner the damper 160 is tuned so as to be biased towards a fully extended position as shown in the figures but to apply resistance to mimic the behavior of human toes while the test fixture 40 is taking a stride.

In the illustrated embodiment, the foot module 60 is passive, and does not include any motors. It is to be understood, however, that in other embodiments the foot module 60 may include one or more motors to control ankle joint 62 motion and forces in any direction as well as toe motion and force application, and can be controlled by the electronic management system 42.

Figure 17:
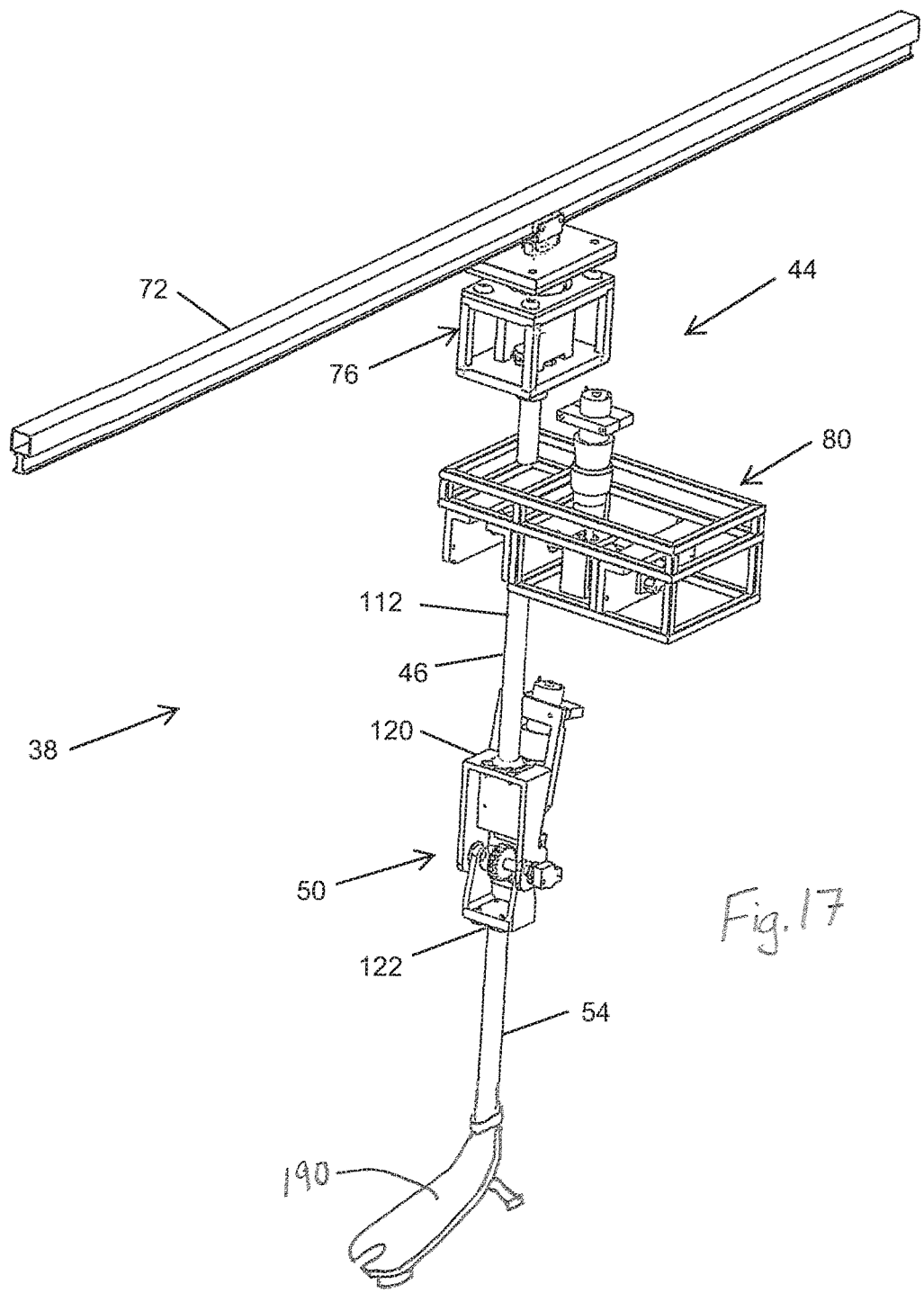
FIG. 17 shows an embodiment in which the test fixture of FIG. 3 has a foot prosthesis mounted thereon for testing.

As discussed above, each of the hip, knee and foot modules 80, 50, 60 include connectors adapted to connect to portions of one or both of the thigh and shin pylons 46, 54. Preferably, such connectors are configured to comply with standard connectors of various prostheses. Thus, the test fixture 40 can be used to test any of multiple prostheses. For example, a knee prosthesis can be attached to the thigh and shin pylons 46, 54 in place of the knee module 50, or a below-knee prosthesis can be attached to the knee module 50 in place of the shin pylon 54 and foot module 60. In FIG. 17, a foot prosthesis 190 is depicted attached to the distal end of the shin pylon 54 in place of the foot module 60.

Additionally, in some embodiments the shin and/or thigh pylons 54, 46 can be configured to have an adjustable length in order to more closely approximate a specific patient's dimensions. In additional embodiments, several pylons of various lengths can be provided, and selectively attached to the test fixture 40 to more closely approximate a specific patient's dimensions.

As discussed above, many sensors, including force sensors, angular location sensors, position sensors or markers, or the like preferably are attached to the test fixture 40. Similarly, multiple sensors can be attached to a prosthesis that is attached to the test fixture 40. As such, during operation of the test fixture 40 as it takes a full stride, sensor data will be collected and sent to the electronic management system 42.

In one preferred embodiment, the electronic management system 42 will operate the test fixture 40 to perform a walking stride in accordance with all the position data of a selected desired gait cycle. In some embodiments desired patient parameters such as weight and height can also be replicated during the test.

In a preferred embodiment, the selected desired gait cycle is the patient's own gait cycle from when he was able-bodied. However, the selected desired gait cycle can also be selected from a database of gait cycles of able-bodied individuals or average gait cycles of able-bodied individuals. Further, the desired gait cycle can be obtained by measuring the gait cycle of the patient's own able-bodied lower limb and mirroring that gait cycle to determine the desired gait cycle.

As also discussed above, an ill-fitting prosthesis may alter an amputee patient's stride so that unnatural forces are applied to the patient's able joints. Over time, such forces can cause substantial damage to the joint and pain for the patient. Thus, forces measured during a test help a clinician determine the suitability of the tested prosthesis for the patient. In accordance with one embodiment, after a proposed prosthesis has been tested, force sensor data indicating forces experienced by the test fixture 40 joints are evaluated to determine whether they fall within an acceptable range of forces for that particular joint. In some instances a target force for a particular direction on a particular joint may be zero, but a range of a number of pounds of force around the target may be acceptable. In other instances, target forces may be nonzero, and acceptable ranges of forces can be determined based upon experience.

In a preferred embodiment, to properly size a lower limb prosthesis for a specific patient, a clinician may review patient data and select a desired gait cycle that best matches the patient. The clinician may also select a proposed prosthesis for testing. After testing, the clinician will review sensor data to gauge compliance with acceptable ranges of forces for particular joints. Acceptable ranges of angular data may also be evaluated, both of the test fixture 40 and of the prosthesis itself to determine whether the sensor data from the test falls within acceptable operational ranges. If one or more sensed measurement falls outside a range of compliance the clinician may either select a different prosthesis or make an adjustment to the proposed prosthesis, after which the clinician may run another test. In this manner a clinician may use objective data to iteratively tune a prosthesis to a patient.

Figure 18:
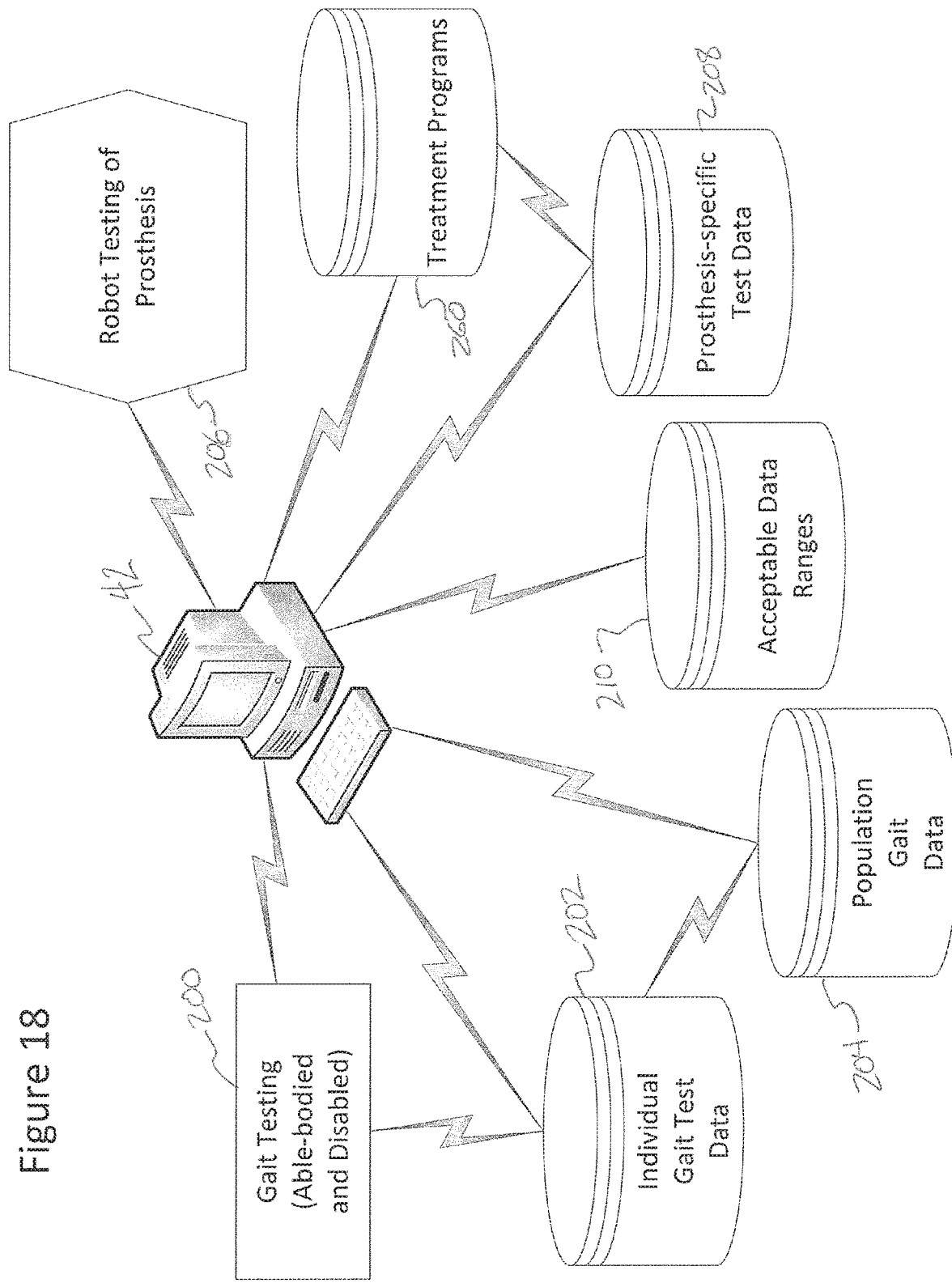
FIG. 18 is a chart depicting the interrelationships of various data.

With reference to FIG. 18, in some embodiments, able-bodied individuals undergo gait cycle testing 200 in order to obtain kinematic, position and force data corresponding to the gait cycle for their able-bodied stride. Test data can be saved for that individual, and can also contribute to a database 202, 204 of test data for able-bodied individuals. Such test data can be categorized, such as by gender, height, weight, age, dimensions of leg segments, health, athleticism, etc.

Disabled individuals can also undergo gait cycle testing 206. Typically they will wear a prosthesis in such testing, which can record measurements relating to the gait cycle of the disabled leg, and also the gait cycle of the able-bodied leg. Gait cycle data can be saved in individual and population gait cycle databases 202, 204. Also, gait cycle testing data can be saved in prosthesis-specific databases 206, tied to a particular prosthesis 208, and qualified by data about the patient such as weight, height, age, health, complaints regarding fit, discomfort, ancillary joint problems, etc. As such, a history of problems with particular prostheses, as well as a pattern of a particular prosthesis's strengths and weaknesses, and patterns of the type of people it works best with, can be accumulated. In this manner, ranges of acceptable (healthy) forces, angular position and the like can be established.

Testing can also be performed for well-fitting prostheses that are comfortable and do not lead to damage to amputee patients' able-bodied joints. Testing such prostheses will help to further define the ranges of acceptable forces, angular position and the like. Such acceptable ranges can be provided to a database 210.

Figure 19:
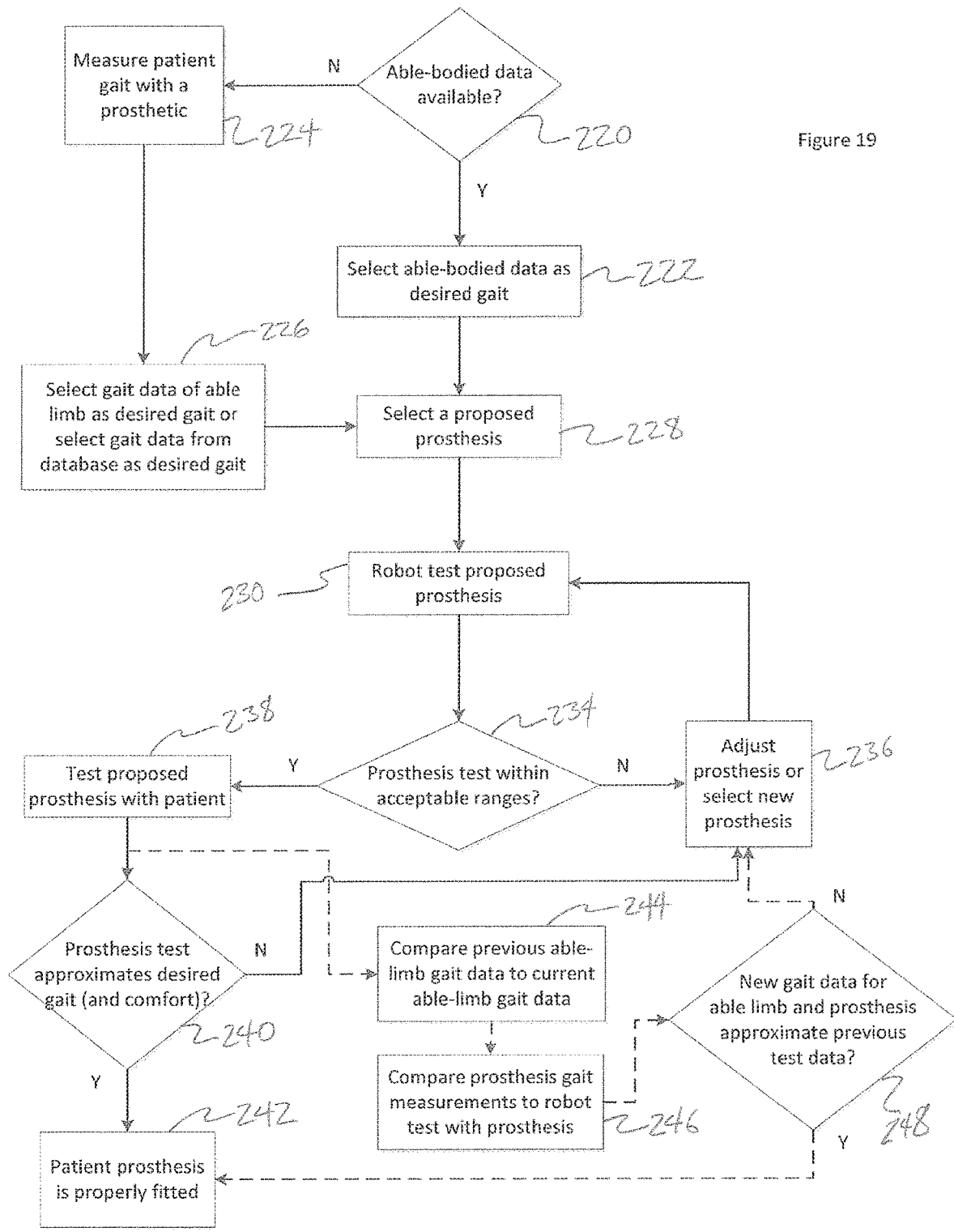
FIG. 19 depicts a method of using the test fixture for fitting a prosthesis.

FIG. 19 presents an embodiment of a method for fitting a lower-limb prosthesis to a patient. If able-bodied gait cycle data 220 for the patient is available, the able-bodied data is selected 222 as a desired gait. If able-bodied data is not available, the patient can be given a temporary prosthesis, and gait data can be measured 224, including data concerning the patient's able limb. Preferably the gait of the able limb is selected as a desired gait 226.

Based on the technician's experience, manufacturer specifications, the selected gait data, and/or prosthesis-specific gait cycle data, a technician selects a proposed prosthesis 228. The proposed prosthesis is tested 230 by the robot leg test fixture 40 with other parameters (height, weight, etc.) of the patient considered and applied by the electronic management system 42. In the test, the test fixture 40 will take a walking stride in accordance with the desired gait cycle. Data such as forces on test fixture joints or the prosthesis and also angular position data are examined to see if the data is within acceptable parameters defining a well-fitting prosthetic 234. As discussed above, if the test fixture 40 reveals data that does not fall within the desired force or angular parameters, the technician either adjusts the prosthesis 236 (with identification of areas of adjustment generally made apparent from the test data) or may select a different prosthesis. Testing and comparing is then repeated iteratively until the proposed prosthesis complies with acceptable force and angular parameters during tests.

Once a proposed prosthesis appears to conform with acceptable parameters, the patient can be brought in to test the proposed prosthesis in person 238. If the prosthesis is comfortable, and/or if the prosthesis (as worn by the patient) is measured during patient gait testing 240 and determined to have a gait cycle consistent with the selected desired gait cycle, the patient is considered properly fitted to the prosthesis 242. In this manner, a patient can be fitted with a prosthesis based on objective measurements rather than subjective judgments. Also, a proposed prosthesis can be prepared and adjusted prior to the patient coming in, further streamlining the fitting process.

If, when fitted with the prosthesis, the patient is measured via gait cycle testing, and does not have a gait cycle that approximates the selected desired gait cycle, or if the prosthesis is uncomfortable, the technician may again adjust the proposed prosthesis, or select a new prosthesis 236, and go through the iterative testing program again.

Continuing with reference FIG. 19, in some embodiments, when the proposed prosthesis is tested with the actual patient, the patient's able-limb gait cycle while wearing the proposed prosthesis will be tested and compared to the patient's able-limb gait cycle with the temporary prosthesis from the previous test 244. Also, the prosthesis-side gait cycle measurements will be compared to the gait cycle measurements from the test fixture test 246. If such new gait data for the able limb and/or prosthesis do not approximate prior test data 248, the technician may make further adjustments, or a different prosthesis may be selected 236. Through further selections and testing, a prosthesis can be selected and adjusted to provide gait cycle data approaching the patient's natural or desired gait. Of course, in some embodiments, a desired gait cycle can be selected from a database of average gait cycles of comparable patients.

Figure 20:
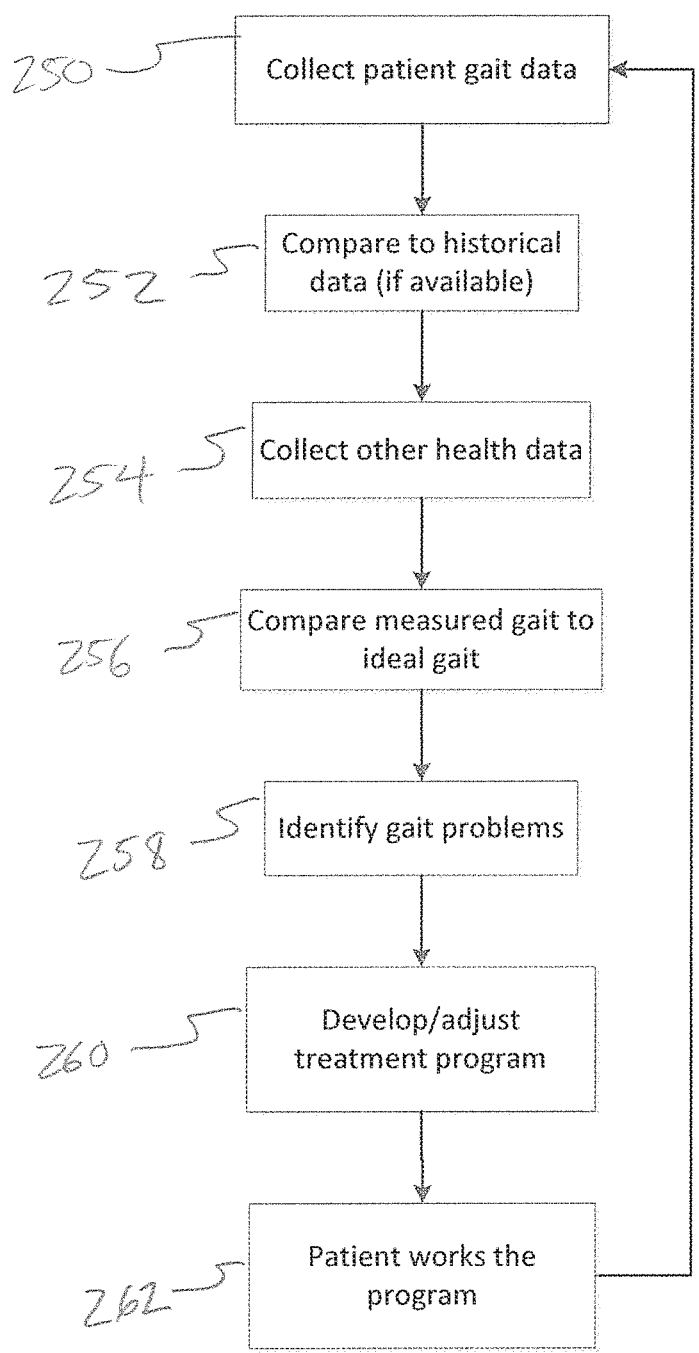
FIG. 20 depicts a method of treating gait problems in accordance with another embodiment.

With reference next to FIG. 20, gait cycle data can be used to treat various gait problems, both for amputees and able-bodied people. This may include able-bodied people that have been injured or have gait problems from other causes, and need physical therapy. In some cases athletes seeking to improve or optimize their gait cycle may seek such treatment. In such embodiments, a clinician may have a sensor apparatus to collect gait cycle data of the patient 250. The clinician may have access to and interact with databases such as in FIG. 18, to store patient gait data and to access population gait cycle data.

If the patient has historical gait data, such as his own able-bodied gait cycle data (for example from before an accident), the patient's current gait cycle data can be compared to the historical data 252. Also, other health problems, particularly problems such as back pain, hip pain, etc., which can be related to or affect gait, can be investigated 254. The clinician can determine an ideal gait cycle, and can compare the current gait cycle to the ideal gait cycle 256. Such a comparison can help identify gait problems 258. Additionally, or alternatively, upon entering patient data, servers in the cloud having access to gait cycle databases can calculate an ideal or desired gait cycle for the patient. A treatment program 260 (see FIG. 18) can be developed, including goal waypoints for the patient's gait cycle, and even suggesting apparatus (such as braces or wraps) or exercises (such as for targeted strengthening) to help the patient achieve an ideal or goal gait cycle. For prosthesis-wearing individuals, the treatment program may include a suggested adjustment to the prosthesis that may urge or force the patient to develop new, healthier, walking habits.

The patient may then work the program 262. Periodically, the patient's gait cycle data will be remeasured, and the patient will be reevaluated for progress in the treatment program, and adjustments to the treatment program may be made. The patient's progress can be maintained in the cloud-based server and database. Levels of treatment success can also be maintained in databases to help improve treatment prescriptions for future patients.

The embodiments discussed above have provided a good context for disclosing and discussing inventive subject matter. Other embodiments may employ different specific structural shapes and interactions. For example, the above discussion focusses on lower-limb prostheses. Such prostheses can include foot-only, foot and shin, knee, and above or below-knee prostheses, and even can apply to treatment of able-bodied individuals. These principles may also apply to other limbs and motion, such as arm motions.

Also, it is to be understood that the particular structure of the test fixture 40 discussed above has been given by example only. Other specific structures can be employed to practice the principles of the invention. It is therefore anticipated that various types and styles of test fixture 40s can yield force sensor data, angular data, or other types of data that will help the clinician determine how well a prosthesis will fit a patient having a particular set of physical parameters.

The embodiments discussed above have disclosed structures with substantial specificity. This has provided a good context for disclosing and discussing inventive subject matter. However, it is to be understood that other embodiments may employ different specific structural shapes and interactions.

Although inventive subject matter has been disclosed in the context of certain preferred or illustrated embodiments and examples, it will be understood by those skilled in the art that the inventive subject matter extends beyond the specifically disclosed embodiments to other alternative embodiments and/or uses of the invention and obvious modifications and equivalents thereof. In addition, while a number of variations of the disclosed embodiments have been shown and described in detail, other modifications, which are within the scope of the inventive subject matter, will be readily apparent to those of skill in the art based upon this disclosure. It is also contemplated that various combinations or subcombinations of the specific features and aspects of the disclosed embodiments may be made and still fall within the scope of the inventive subject matter. Accordingly, it should be understood that various features and aspects of the disclosed embodiments can be combined with or substituted for one another in order to form varying modes of the disclosed inventive subject matter. Thus, it is intended that the scope of the inventive subject matter herein disclosed should not be limited by the particular disclosed embodiments described above, but should be determined only by a fair reading of the claims that follow.

What is claimed is:

1. A prosthesis fitting apparatus configured to predict the forces exerted on able joints of a user using a prosthesis, comprising:
   a test fixture comprising a hip module and a knee module, the hip module connected to the knee module by an elongate thigh pylon, the knee module configured so that the prosthesis can be releasably attached thereto;
   an electronic controller having access to a desired gait cycle data, the desired gait cycle data comprising a dataset of positions of components of a human lower limb during a complete gait cycle;
   the hip module comprising a hip joint configured to mimic movement of a human hip, the hip module comprising one or more hip motors electronically connected to the electronic controller and configured to move the hip joint in a manner directed by the electronic controller;
   the knee module comprising a knee joint configured to mimic movement of a human knee, the knee module comprising one or more knee motors electronically connected to the electronic controller and configured to move the knee joint in a manner directed by the electronic controller;
   the electronic controller having access to a desired force parameter data, the desired force parameter data comprising acceptable ranges of forces at the hip joint and the knee joint during a gait cycle, the acceptable ranges of forces based on ranges of forces exerted on an able hip joint and an able knee joint during an able gait cycle;
   the test fixture being configured to complete the gait cycle in a manner directed by the electronic controller while the prosthesis is releasably attached thereto, the electronic controller configured to direct the hip and knee motors to mimic the desired gait cycle data when the prosthesis is attached to the test fixture; and
   a plurality of force sensors attached to the test fixture at or adjacent one or more of the hip joint and knee joint, the force sensors configured to measure forces exerted on the test fixture at the one or more of the hip joint and knee joint when the test fixture completes the gait cycle as directed by the electronic controller so as to measure the forces exerted on the hip and knee joints during use of the prosthesis, and to communicate a measured force data to the electronic controller; and
   wherein the electronic controller is configured to compare the measured force data to the desired force parameter data and determine whether the measured force data is within the acceptable ranges of the desired force parameter data.

2. The prosthesis fitting apparatus as in claim 1, wherein the knee module is releasably attachable to a proximal end of an elongate shin pylon, and a distal end of the elongate shin pylon is releasably attachable to a foot prosthesis.

3. The prosthesis fitting apparatus as in claim 2 additionally comprising a foot module comprising an ankle joint, the foot module being configured so that the ankle joint mimics the movement of a human ankle, and wherein the distal end of the elongate shin pylon is releasably attachable to the foot module.

4. The prosthesis fitting apparatus as in claim 2, wherein a length of one or more of the thigh and shin pylons can be adjusted.

5. The prosthesis fitting apparatus as in claim 1, wherein the test fixture is configured to mimic a patient weight associated with the desired gait cycle data.

6. A testing apparatus for predicting the forces exerted on able joints during use of a lower-body prosthesis, comprising:
   a hip module and a knee module, the hip module releasably connected to the knee module by an elongate thigh pylon, a shin pylon extending from the knee module and configured so that a prosthesis can be attached thereto, the thigh pylon also configured to selectively accept the prosthesis attached thereto in lieu of the knee module;
   the hip module comprising a hip joint and one or more hip motors, the hip motors configured to move components of the hip module so that the hip joint can mimic movement of an able human hip;
   the knee module comprising a knee joint and one or more knee motors, the knee motors configured to move components of the knee module so that the knee joint can mimic movement of an able human knee;
   an electronic controller spaced from the hip module and the knee module and selectively electronically connectable to the one or more hip motors and the one or more knee motors and being configured to communicate control instructions to the one or more hip motors and one or more knee motors;
   the electronic controller having access to a desired gait cycle data, the desired gait cycle data comprising a dataset of positions and relative positions of able human hip joints and able human knee joints during an able gait cycle;
   the electronic controller having access to a desired force parameter data, the desired force parameter data comprising acceptable ranges of forces for the hip joint and the knee joint, the acceptable ranges of forces selected so that when a force within the acceptable ranges of forces is repeatedly exerted on an able human hip joint and/or an able human knee joint during an able gait cycle, will minimize the likelihood of injury to the corresponding joint;

the testing apparatus being configured to complete a gait cycle in a manner directed by the electronic controller while the prosthesis is releasably attached thereto and in which the prosthesis contacts a floor during a portion of the gait cycle, the electronic controller configured to direct the hip and knee motors to mimic the positions defined in the desired gait cycle data when the prosthesis is attached to the testing apparatus and completing the gait cycle; and a hip force sensor attached to the testing apparatus at or adjacent the hip joint, the hip force sensor configured to measure forces exerted on the testing apparatus at the hip joint when the testing apparatus completes a gait cycle as directed by the electronic controller so as to measure force exerted on the hip joint during use of the prosthesis, and to communicate a measured hip force data to the electronic controller;

wherein the electronic controller is configured to compare the measured hip force data to desired force parameter data for the hip and to determine whether the measured hip force data is within the acceptable ranges of the desired force parameter data for the hip.

7. The testing apparatus as in claim 6, additionally comprising a knee force sensor attached to the testing apparatus at or adjacent the knee joint, the knee force sensor configured to measure force exerted on the testing apparatus at the knee joint when the testing apparatus completes a gait cycle as directed by the electronic controller so as to measure force exerted on the knee joint during use of the prosthesis, and to communicate a measured knee force data to the electronic controller;

wherein the electronic controller is configured to compare the measured knee force data to desired force parameter data for the knee and to determine whether the measured knee force data is within the acceptable ranges of the desired force parameter data for the knee.

8. The testing apparatus as in claim 6, wherein a length of the thigh pylon and a length of the shin pylon can be adjusted to approximate a thigh length or shin length, respectfully, of a prospective user of the prosthetic.

* * * * *